(12) United States Patent
Rege et al.

(10) Patent No.: US 11,020,015 B2
(45) Date of Patent: Jun. 1, 2021

(54) SYSTEM AND METHOD FOR RAPID EXAMINATION OF VASCULATURE AND PARTICULATE FLOW USING LASER SPECKLE CONTRAST IMAGING

(71) Applicant: VASOPTIC MEDICAL, INC., Baltimore, MD (US)

(72) Inventors: Abhishek Rege, Baltimore, MD (US); M. Jason Brooke, University Park, MD (US); Kartikeya Murari, Calgary (CA); Yusi Liu, Rockville, MD (US)

(73) Assignee: Vasoptic Medical, Inc., Baltimore, MD (US)

( * ) Notice: Subject to any disclaimer, the term of this patent is extended or adjusted under 35 U.S.C. 154(b) by 437 days.

(21) Appl. No.: 15/767,057

(22) PCT Filed: Oct. 7, 2016

(86) PCT No.: PCT/US2016/055976
§ 371 (c)(1),
(2) Date: Apr. 9, 2018

(87) PCT Pub. No.: WO2017/062759
PCT Pub. Date: Apr. 13, 2017

(65) Prior Publication Data
US 2018/0296103 A1    Oct. 18, 2018

Related U.S. Application Data

(60) Provisional application No. 62/239,529, filed on Oct. 9, 2015.

(51) Int. Cl.
*A61B 5/026* (2006.01)
*G02B 27/48* (2006.01)
(Continued)

(52) U.S. Cl.
CPC .......... *A61B 5/0261* (2013.01); *A61B 3/1233* (2013.01); *A61B 5/0066* (2013.01);
(Continued)

(58) Field of Classification Search
CPC ....... A61B 3/0075; A61B 3/0083; A61B 3/12; A61B 3/1208; A61B 3/1233; A61B 3/14;
(Continued)

(56) References Cited

U.S. PATENT DOCUMENTS 6,419,627 B1    7/2002  Ben Nun
9,492,083 B2 *  11/2016 Rege .................... A61B 3/1233
(Continued)

FOREIGN PATENT DOCUMENTS

WO    2014151114 A1    9/2014

OTHER PUBLICATIONS

European Search Report dated Jun. 17, 2019 in European Patent Application No. 16854417.9.

*Primary Examiner* — Mark D Remaly
(74) *Attorney, Agent, or Firm* — Pierce Atwood LLP

(57) ABSTRACT

Examination of the structure and function of blood vessels is an important means of monitoring the health of a subject. Such examination can be important for disease diagnoses, monitoring specific physiologies over the short- or long-term, and scientific research. This disclosure describes technology and various embodiments of a system and method for imaging blood vessels and the intra-vessel blood flow, using at least laser speckle contrast imaging, with high speed so as to provide a rapid estimate of vessel-related or blood flow-related parameters.

26 Claims, 7 Drawing Sheets

(51) Int. Cl.
      *A61B 5/00*    (2006.01)
      *A61B 5/02*    (2006.01)
      *A61B 3/12*    (2006.01)
      *A61B 3/14*    (2006.01)
      *A61B 3/00*    (2006.01)

(52) U.S. Cl.
      CPC ............... *A61B 5/02* (2013.01); *A61B 5/721* (2013.01); *A61B 5/7207* (2013.01); *A61B 5/742* (2013.01); *G02B 27/48* (2013.01); *A61B 3/0075* (2013.01); *A61B 3/0083* (2013.01); *A61B 3/12* (2013.01); *A61B 3/1208* (2013.01); *A61B 3/14* (2013.01)

(58) Field of Classification Search
      CPC ....... A61B 5/0066; A61B 5/02; A61B 5/0261; A61B 5/7207; A61B 5/721; A61B 5/742; G02B 27/48
      See application file for complete search history.

(56) References Cited

U.S. PATENT DOCUMENTS

2003/0152519 A1    8/2003   Koenig et al.
2012/0277849 A1    11/2012  Tani et al.

\* cited by examiner

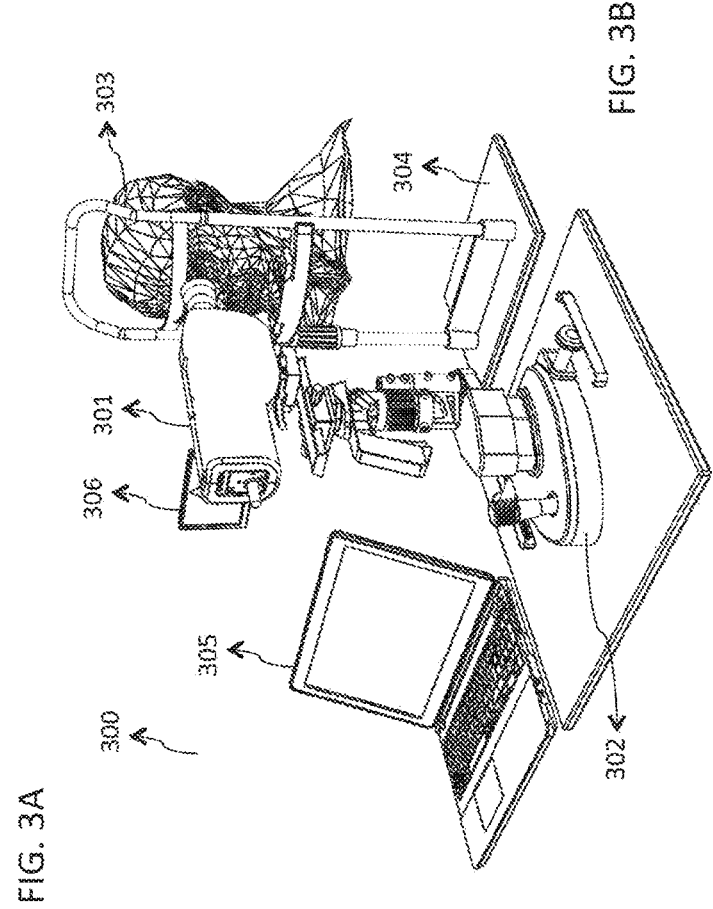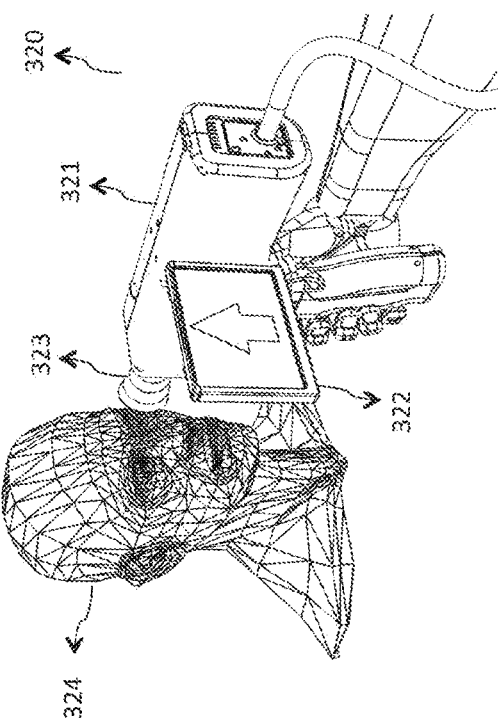

SYSTEM AND METHOD FOR RAPID EXAMINATION OF VASCULATURE AND PARTICULATE FLOW USING LASER SPECKLE CONTRAST IMAGING

RELATED APPLICATIONS

This application is a National Stage application under 35 U.S.C. 371 of PCT International Application No. PCT/US2016/055976, filed Oct. 7, 2016, which claims the benefit of U.S. Provisional Application No. 62/239,529, filed Oct. 9, 2015 the entire disclosure of which is hereby incorporated by reference herein.

GOVERNMENT GRANT SUPPORT

This invention was made with government support under grant 1R43EB019856-01A1 awarded by the National Institute of Biomedical Imaging and Bioengineering (of the National Institutes of Health). The government has certain rights in the invention.

FIELD OF THE INVENTION

The present invention relates generally to vascular imaging technologies and methods and, more particularly, to the rapid examination of vasculature and blood flow using laser speckle contrast imaging.

BACKGROUND

Blood vessels are the fundamental mechanism by which human and animal biological systems and related tissues, organs, and organ systems receive nutrient supply and remove waste products to maintain its viability, integrity, and functionality. Anatomical characteristics of blood vessels (e.g., size, structure, orientation, location, quantity, distribution, and type) are specific to each biological system, tissue, organ, or organ system. Many pathologies manifest as changes in these anatomical characteristics and are also accompanied by changes in vascular physiology (e.g., velocity or flow rates of blood within an individual vessel, group of vessels, or network of vessels; distribution of blood flow within a group or network of connected or independent vessels, including regions of vascular profusion and non-perfusion; and vessel compliance, contractility, and proliferation). For example, diabetic retinopathy (DR) is a vision-threatening complication of diabetes that manifests as progressive narrowing of arteriolar caliber until occlusion occurs. Vessel occlusion is typically followed by vessel proliferation (i.e., angiogenesis), which results in increased vision loss and progression toward blindness. Numerous other diseases and conditions involve pathologies or symptoms that manifest in blood vessel anatomy or physiology. Diseases associated with modified or abnormal vasculature in the eye include DR, hypertensive retinopathy (HR), glaucoma, age-related macular degeneration (AMD), retinopathy of prematurity (ROP), and choroidal neovascularization (CNV), among others. Vascular changes in the eye are also associated with systemic diseases, including sleep apnea. Alzheimer's disease, brain lesions (e.g., stroke), various complications of cardiovascular disease, and metabolic diseases (e.g., diabetes and hyperthyroidism). Various dermatological diseases and conditions, including melanoma, diabetic foot ulcers, skin lesions, wounds, and burns, involve injury to or pathophysiology of the vasculature.

These anatomical and physiological characteristics are important for the development of novel diagnostics and therapeutics; the diagnosis, management, and treatment of many diseases and medical conditions; and the advancement of standard of care for patients (human and animal). By evaluating the anatomical and physiological characteristics of the vasculature (directly or indirectly, quantitatively or qualitatively), a scientist, clinician, or veterinarian can begin to understand the viability, integrity, and functionality of the biological system, tissue, organ, or organ system being studied. Depending on the specific condition being studied, important markers may manifest as acute or long-term alterations in blood flow or other anatomical and physiological characteristics of the vasculature. For example, anatomical and physiological information, in either absolute terms or as relative changes, may be used as a mechanism for monitoring and assessing changes in the retinal vasculature to determine the risk of blindness associated with DR, the likely onset of visual impairment, and potential disease management and treatment options, among other things. Likewise, almost all types of tumors are accompanied by vascular changes to the cancerous tissue; tumor angiogenesis and increased blood flow is often observed in cancerous tissue due to increased metabolic demand of the tumor cells. Similar vascular changes are associated with healing of injuries, including wounds and burns, where angiogenesis serves a critical role in the healing process. Hence, anatomical and physiological information may assist a clinician or veterinarian in the monitoring and assessment of healing after a severe burn, recovery of an incision site, or the effect of a therapeutic agent or other type of therapy (e.g., skin graft or negative pressure therapy) in the treatment of a wound or diabetic foot ulcer.

Monitoring and assessment of anatomical and physiological information can be critically important for surgical procedures. The imaging of blood vessels, for example, can serve as a basis for establishing landmarks during surgery. During brain surgery, when a craniotomy is performed, the brain often moves within the intracranial cavity due to the release of intracranial pressure, making it difficult for surgeons to use preoperatively obtained images of the brain for anatomical landmarks. In such situations, anatomical and physiological information may be used by the surgeon as vascular markers for orientation and navigation purposes. Anatomical and physiological information also provides a surgeon with a preoperative, intraoperative, and postoperative mechanism for monitoring and assessment of the target tissue, organ, or an individual blood vessel within the surgical field.

The ability to quantify, visualize, and assess anatomical and physiological information in real-time or near-real-time can provide a surgeon with feedback to support diagnosis, treatment, and disease management decisions. An example of a case where real-time feedback regarding anatomical and physiological information is important is that of intraoperative monitoring during neurosurgery, or more specifically, cerebrovascular surgery. The availability of real-time blood flow assessment in the operating room (OR) allows the operating neurosurgeon to guide surgical procedures and receive immediate feedback on the effect of the specific intervention performed. In cerebrovascular neurosurgery, real-time blood flow assessment can be useful during aneurysm surgery to assess decreased perfusion in the feeder vessels as well as other proximal and distal vessels throughout the surgical procedure.

Likewise, rapid examination of vascular anatomy and physiology has significant utility in other clinical, veterinary, and research environments. For example, blood flow is often commensurate with the level of activity of a tissue and related organ or organ system. Hence, vascular imaging techniques that can provide rapid assessment of blood flow can be used for functional mapping of a tissue, organ, or organ system to, for example, evaluate a specific disease, activity, stimulus, or therapy in a clinical, veterinary, or research setting. To illustrate, when the somatosensory region of the brain is more active because of a stimulus to the hand, the blood flow to the somatosensory cortex increases and, at the micro-scale, the blood flow in the region of the most active neurons increases commensurately. As such, a scientist or clinician may employ one or more vascular imaging techniques to evaluate the physiological changes in the somatosensory cortex associated with the stimulus to the hand.

A number of vascular imaging approaches exist to evaluate anatomical and physiological information of the tissue vasculature. Magnetic resonance imaging (MRI), x-ray or computerized tomography (CT), ultrasonography, laser speckle contrast imaging (LSCI), and positron emission tomography (PET) are among a number of imaging techniques that offer quantitative and qualitative information about the vascular anatomy and physiology. Each technique offers unique features that may be more relevant to the evaluation of a particular biological system, tissue, organ, or organ system or a specific disease or medical condition.

LSCI has particular relevance in the rapid, intraoperative examination of vascular anatomy and physiology. LSCI is an optical imaging technique that uses interference patterns (called speckles), which are formed when a camera captures photographs of a rough surface illuminated with coherent light (e.g., a laser), to estimate and map flow of various particulates in different types of enclosed tubes. If the rough surface comprises moving particles, then the speckles corresponding to the moving particles cause a blurring effect during the exposure time over which the photograph is acquired. The blurring can be mathematically quantified through the estimation of a quantity called laser speckle contrast (K), which is defined as the ratio of standard deviation to mean of pixel intensities in a given neighborhood of pixels. The neighborhood of pixels may be adjacent in the spatial (i.e., within the same photograph) or temporal (i.e., across sequentially acquired photographs) domains or a combination thereof. In the context of vascular imaging, LSCI quantifies the blurring of speckles caused by moving blood cells within the blood vessels of the illuminated region of interest (ROI) and can be used to analyze detailed anatomical information (which includes but is not limited to vessel diameter, vessel tortuosity, vessel density in the ROI or sub-region of the ROI, depth of a vessel in the tissue, length of a vessel, and type of blood vessel, e.g., its classification as artery or vein) and physiological information (which includes but is not limited to one or more of blood flow and changes thereof in the ROI or a sub-region of the ROI, blood flow in an individual blood vessel or group of individual blood vessels, and fractional distribution of blood flow in a network of connected or disconnected blood vessels).

While non-LSCI methods of intraoperative real-time blood flow assessment are currently used, no single method is considered adequate in all scenarios. For example, in the context of cerebrovascular surgery such as aneurysm surgery, imaging of small yet important vessels called perforators necessitates a high-resolution imaging technique for monitoring anatomical and physiological information, which is currently unavailable in the neurosurgical OR. The use of Indocyanine Green (ICG) Videoangiography has been assessed for this purpose but challenges still remain because of the potential for dye leakage. Intraoperative angiography is currently considered the gold standard to assess vessel patency following a number of cerebrovascular procedures (e.g., aneurysm clipping and arteriovenous malformation. AVM, obliteration). However, angiography does not provide real-time assessment during the actual performance of surgery. Furthermore, given the invasive nature of this technique, and despite advancements, the risk of complications is not eliminated. In AVM surgery, real-time blood flow assessment helps the surgeon better understand whether particular feeding vessels carry high flow or low flow, which could ultimately impact the manner in which those vessels are disconnected from the AVM (i.e., bipolar cautery versus clip ligation). Finally in a disease such as Moyamoya, which may require direct vascular bypass, real-time flow assessment can be useful in identifying the preferred recipient vessels for the bypass as well as assessing the flow in that bypass and surrounding cortex once the anastomosis is completed.

The real-time assessment of blood flow may be helpful in other surgery fields that rely on vascular anastomoses as well, specifically plastic surgery, vascular surgery, and cardiothoracic surgery. Currently, technology such as the use of Doppler ultrasonography is used to confirm the patency of an anastomosis. However, real-time, quantitative imaging can add a tremendous benefit in assessing the adequacy of a bypass, revealing problems to the surgeon in real time to facilitate correction during surgery rather than postoperatively when either it is too late or the patient requires a reoperation.

LSCI has been used as a blood flow monitoring technique in the OR. LSCI has been considered for functional mapping in awake craniotomies to prevent damage to eloquent regions of the brain, to assess the surgical shunting of the superior temporal artery (STA) and the middle cerebral artery (MCA) and for intraoperative monitoring during neurosurgery. These approaches have limitations of spatio-temporal resolution and availability of anatomical and physiological information on a real-time or near-real-time basis.

SUMMARY OF THE INVENTION

This disclosure relates to technology and various embodiments of a system for rapid examination (i.e., real-time or near-real-time) of vasculature and particulate flow using LSCI. In various embodiments, the system comprises at least one illumination module and at least one light manipulation component to illuminate the ROI of a target tissue, at least one camera module and at least one optical element for capturing light reflected from the ROT of a target tissue, at least one processor that is programmed to calculate, estimate, and/or determine anatomical and physiological information in real-time or near-real-time using at least LSCI, at least one storage module for short- and long-term access or archival of electronic data captured, acquired and/or generated by the system, and at least one display module that presents the anatomical and physiological information in real-time or near-real-time.

In various embodiments, the at least one light source comprises at least one coherent light. In some embodiments, the at least one light source comprises at least one coherent light and one or more non-coherent or partially coherent light. In various embodiments, the at least one light manipulation component comprises lenses, mirrors, apertures, filters, beam splitters, beam shapers, polarizers, wave retarders, and fiber optics. In various embodiments, the target tissue comprises the cornea, sclera, retina, epidermis, dermis, hypodermis, skeletal muscle, smooth muscle, cardiac muscle, cerebrovascular tissue, the stomach, large and small intestines, pancreas, liver, gallbladder, kidneys, and lymphatic tissue. In various embodiments, the target tissue is in situ, in vivo, or in vitro. In various embodiments, the at least one camera module comprises a charge coupled device (CCD), complementary metal oxide semiconductor (CMOS), metal oxide semiconductor (MOS), or phototubes. In various embodiments, the at least one optical element comprises lenses, mirrors, apertures, filters, beam splitters, beam shapers, polarizers, wave retarders, and fiber optics. In various embodiments, the at least one processor comprises a field programmable gate array (FPGA); the central processing unit of a personal computer, laptop computer, mobile computing platform, remote server or server system; an off-the-shelf microprocessor; or equivalent computing device. The at least one processor may also comprise a graphics processing unit (GPU), a specialized processor configured for handling graphical and image data. The processor may operate a single or multiple cores and carry out serial or parallel computations. In various embodiments, the anatomical information includes, but is not limited to, size (e.g., diameter and length), structure (e.g., thickness and tortuosity), orientation (e.g., depth in the tissue, relative relation to other anatomical features within the ROI), location (e.g., relative relation to other anatomical features within the organ, organ system, or biological system), quantity, distribution (e.g., density in the ROI or sub-region of the ROI), and type of blood vessels (e.g., artery, arteriole, vein, venule, or other classification). In various embodiments, the physiological information includes, but is not limited to, velocity or flow rates of blood within an individual vessel, group of vessels, or network of vessels; distribution of blood flow within a group or network of connected or independent vessels, including regions of vascular profusion and nonperfusion; and vessel compliance, contractility, and proliferation. In various embodiments, the calculating, estimating, and determining in real-time comprises performing a processing step within 40 milliseconds of the original event that triggered the processing step. In various embodiments, the calculating, estimating, and determining in near-real-time comprises performing a processing step between 40 milliseconds and 1000 milliseconds of the original event that triggered the processing step. In various embodiments, generating an LSCI image comprises at least the calculation of laser speckle contrast values at one or more pixels of interest by utilizing the intensities of pixels in a spatial, temporal, or spatio-temporal neighborhood around the one or more pixels of interest; and may also comprise estimation of speckle contrast-derived secondary values that can be utilized in estimation of anatomical and physiological information local to the feature at the one or more pixels of interest. In various embodiments, the at least one storage device comprises random access memory (RAM) units, flash-based memory units, magnetic disks, optical media, flash disks, memory cards, or external server or system of servers (e.g., a cloud-based system) that may be accessed through wired or wireless means. In various embodiments, the electronic data comprises raw image data captured by the at least one camera sensor, anatomical and physiological information or equivalent parameters calculated from the raw or processed image data, patient-specific data manually entered or automatically acquired from another source (e.g., electronic health record, electronic medical record, personal health record, picture archiving and communications system, PACS, or other sensors, including heart rate monitor, finger plethysmograph, respirator, or other surgical, anesthesiological, or medical equipment), derivative data associated with the processing of these electronic data, or control and guidance information (e.g., scale bars, menu options, operating instructions, error messages) or a combination thereof. In various embodiments, the at least one display device comprises a digital or analog 2-dimensional or 3-dimensional presentation system (e.g., television, computer monitor, head-mounted display, or mobile computing platform screen) based on various technologies (e.g., cathode ray tubes, light-emitting diodes, plasma display technology, liquid crystals display technology, or carbon nanotubes). In some embodiments, the at least one display device presents electronic data, including the anatomical and physiological information or equivalent parameters calculated from the raw or processed image data, in a manner that allows an observer to visualize the information, parameters, or electronic data overlaid on the FOV of the target tissue. In some embodiments, the system is designed to present electronic data, including the anatomical and physiological information or equivalent parameters calculated from the raw or processed image data, to the user via the viewing lens of the system, an associated microscope, or other surgical instrument.

This invention further relates to technology and methods for rapid examination of vasculature and particulate flow using LSCI. To produce LSCI data, a stack of N image frames is captured under coherent illumination and speckle contrast $K(P_0)$ is calculated at every pixel of interest $P_0$ using Eq. 1.

$$K(P_0) = \sigma_{\mathbb{N}(P_0)}/\mu_{\mathbb{N}(P_0)} \qquad \text{Eq. 1}$$

where $\sigma\mathbb{N}_{(P_0)}$ and $\mu\mathbb{N}_{(P_0)}$ are the standard deviation and mean, respectively, in the intensity of all pixels on a defined local neighborhood $\mathbb{N}(P_0)$. $K(P_0)$ values can be calculated such that $\mathbb{N}(P_0)$ is chosen exclusively in either the spatial domain called sLSCI (Eq. 2a) or the temporal domain called tLSCI (Eq. 2b).

$$\mathbb{N}_{(P_0)} = \{P(x,y,n_0) \text{ s.t. } \|(x,y,n_0)-(x_0,y_0,n_0)\| \leq 4 \text{ px}\} \qquad \text{Eq. 2a}$$

$$\mathbb{N}_{(P_0)} = \{P(x_0,y_0,n) \text{ s.t. } |n-n_0| \leq 80 \text{ frames}\} \qquad \text{Eq. 2b}$$

In the above equations, x- and y-coordinates represent spatial coordinates, while n represents the temporal placement of the pixel by denoting the frame number in which the pixel is located. Thus, pixel $P_0$ is appropriately represented by the coordinates $(x_0, y_0, n_0)$.

Blood velocity is known to be proportional to a parameter $1/\tau_c$ (where $\tau_c(P_0)$ is the correlation time of intensity fluctuations) that can be computed from $K(P_0)$ using Eq. 3.

$$[K(P_0)]^2 = \frac{\tau_c(P_0)}{T}\left\{2 - \frac{\tau_c(P_0)}{T}\left[1 - \exp\left(-\frac{2T}{\tau_c(P_0)}\right)\right]\right\} \qquad \text{Eq. 3}$$

Thus, plots of $1/\tau_c$ and a plot of $K(P_0)$ are each indicative of blood velocity and flow and potential constituents of anatomical and physiological information. Both these plots can be displayed in grayscale or pseudo-color for visualization purposes.

Spatial processing of speckle data requires only N=1 image frame be acquired and preserves temporal resolution for sequential monitoring, but suffers from a compromised spatial resolution. The degree of compromise in spatial resolution depends on the number of pixels in the spatial neighborhood chosen for calculation of speckle contrast.

For high-resolution LSCI, speckle contrast is calculated using a temporal algorithm that requires the processing of a time-stack of several (typically N=80, but may be different) images. This reduces the temporal resolution of any functional information extracted from the data, and also the prolonged image acquisition time makes the system and method susceptible to motion artifact. Even if images were acquired at 150 frames per second (fps), generating an LSCI image from the 80 frames would require over 0.5 s. To avoid the slow output rate, speckle contrast can be calculated over a rolling time-stack of images—that is by including each new image frame to the processing image stack and removing the oldest image from the stack. This first in first out (FIFO) strategy coupled with fast implementation of speckle contrast calculations allows the output rate to be as high as the camera frame rate but the system would still suffer from latency (i.e., the output would trail the real-time event by a latency of at least the amount of time that is required to acquire the N=80 image frames). If the acquisition speed is 150 fps, the latency corresponding to the acquisition of 80 frames, would be 0.533 seconds.

To counter this problem and achieve rapid examination of vasculature and particulate flow, the subject invention includes a method of calculating speckle contrast using a combination of spatial processing and temporal processing schemes. A pixel-neighborhood that is cuboidal in the spatio-temporal domain is used for calculating speckle contrast. For example, a pixel-neighborhood of 5 pixels×5 pixels×5 frames around it is extracted for every pixel $P_0$ (see Eq. 2) for contrast calculation, as expressed in Eq. 4.

$$N_{(P_0)} = \{P(x,y,n) s \cdot t \cdot \|(x,y)-(x_0,y_0)\| \leq 2 \text{ px and } |n-n_0| \leq 2 \text{ frames}\} \quad \text{Eq. 4}$$

$K(P_0)$ is then calculated using Eq. 1. We have previously demonstrated a field programmable gate array (FPGA) based hardware implementation of temporal contrast calculations. Similar FPGA-based hardware implementations for spatial contrast calculations have also been reported, stLSCI strikes a balance between spatial and temporal resolution while still utilizing adequate number of pixels for robust speckle contrast calculation. The neighborhood in the spatial domain and number of frames used in processing in the temporal domain may be chosen in accordance with the requirements of the imaging application, stLSCI performs on par with sLSCI and tLSCI in reproducibility of speckle contrast values and the ability to discriminate vessels from background tissue. The choice of number of pixels in the spatio-temporal neighborhood may be as few or as many depending on the desired spatio-temporal resolution in the output of imaging and the spatial resolution and frame rate of image acquisition. So, when using a camera operating at 120 Hz, it would be possible to use twice as many frames for stLSCI calculations without compromising the temporal resolution of the output as one would when using a camera operating at 60 Hz. Similarly, choice of the number of pixels in each frame that constitute the spatio-temporal neighborhood would also depend on the spatial resolution at which image acquisition is performed.

Once plots of $1/\tau_c$ or K are obtained, these plots may be processed further to obtain anatomical and physiological information, including:

Blood velocity—Blood velocity may be estimated as a linear or polynomial function of $1/\tau_c$ values at the location. Subsequently, blood perfusion in a region of the ROI may be estimated using these blood velocity estimates.

Vessel diameter—Vessel diameters may be estimated using the appearance of the K or $1/\tau_c$ values within the vessel with respect to those outside the vessel. Comparison of appearance includes comparison of not only the intensities but also the gradient of intensities as well as other features such as ridge-like appearance of vessels or the connectedness of vessels with other vessels. Ridge-like appearance can be formulated using the Hessian matrix and its eigenvalues computed for the LSCI image of the ROI.

Vascular blood flow—Blood flow within blood vessels may be estimated by combining both values of $1/\tau_c$ and value(s) of vessel diameter. In one method, vascular flow may be obtained by integrating the values of blood velocity along the cross-section of the vessel. In another method, vascular flow may be estimated by multiplying the average blood velocity with the diameter of the vessel. Curve fitting may be used to refine the estimates of blood velocity or vessel diameters.

Depth of the vessel in the tissue—Depth of the blood vessel may be estimated using LSCI at multiple different wavelengths, which penetrate the tissue to different extents, thus resolving the vessel based on the appearance of the vessel in the LSCI image obtained at each wavelength relative to its appearance in LSCI images obtained at other wavelengths.

Length of the vessel—Length of the vessel may be estimated by tracking the blood vessel or its centerline at a pixel level from one point to another. The sum of pixel-to-pixel distances may be reported as is, or the pixel-to-pixel distances may be refined to obtain a smooth traversal prior to estimating the total length.

Vessel Tortuosity—Tortuosity of the vessel may be estimated utilizing one of the following methods. One method includes estimation of tortuosity between two locations on any vessel of interest as the ratio of the length of the vessel along its axis between the two locations to the straight line distance between the two locations. Another method includes estimation of tortuosity between two locations on any vessel of interest as the number of times the curvature of the vessel changes per unit length of the vessel while axially traversing the vessel between the said two locations on the vessel.

Type of blood vessel—An artery (or an arteriole) may be discriminated from a vein (or a venule) by analyzing the vessel's appearance in the LSCI image and a colored or monochrome photograph (reflectance or absorption image in non-coherent light). Arterial vessels have higher blood velocities as compared to venous vessels, and also carry more oxygenated blood, which has different light absorption properties.

The subject invention can be embodied differently for different applications that include acute or longitudinal clinical diagnostic and monitoring purposes, clinical decision support, and research uses. In various embodiments, the invention is utilized in a manner such that the target is any enclosed tube (i.e., analogous to blood vessels) and particulate flow (i.e., analogous to blood flow). An example of such a target may be a plastic tube with artificial blood flowing through it, or microfluidic channels with microbeads flowing through them. The lymphatic system is another example of a target that the subject invention may be utilized for imaging.

In various embodiments, the system and method are designed for real-time or near-real-time blood flow imaging during surgery, including cerebrovascular surgery and other neurosurgeries; plastic and reconstructive surgery; ophthalmic surgery; cardiac surgery; endoscopic surgery; ear, nose, and throat (ENT) surgery; and dental surgery. In each case, such assessment of one or more electronic data may lead to actionable outputs such as surgical planning, diagnosis of intended or incidental conditions or complications, prognosis of the outcome of the surgery, modifying the course of the surgery in real-time, short or long-term treatments or therapies, or management of health post-surgery. The actionable output may result from considering the assessment of the one or more electronic data in conjunction with information gathered from other sensory or therapeutic medical device equipment or disease management system.

Cerebrovascular Surgery and Other Neurosurgeries:

In preparation for cerebrovascular surgery, the surgical team establishes a surgical plan, typically based on MRI and CT images of the patient's brain. The surgical plan involves a strategy for navigating to the specific surgical site in a way that minimizes risk of damage to the vascular anatomy. The surgical procedure often requires the use of an operating microscope to observe the surgical field and typically involves observation of vessel patency and vessel-specific physiological information in the surgical field. In an aneurysm surgery, for example, blood flow in perforator vessels associated with the aneurysm and its parent vessels are of great importance for clinical outcomes and, hence, an important monitoring target. Other types of neurosurgeries for which observation of vessel patency and vessel-specific anatomical and physiological information in the surgical field is important include vascular grafting surgeries in patients suffering from Moyamoya disease, arteriovenous malformation surgeries, brain tumor resection surgeries, awake craniotomies where functional mapping is desired, spinal cord surgeries, and surgeries performed to relieve carpel tunnel syndrome. The subject invention can be embodied to provide the surgeon with real-time or near-real-time assessment of vessel patency and vessel-specific anatomical and physiological information to improve the efficiency and effectiveness of cerebrovascular and other neurosurgical procedures.

Plastic and Reconstructive Surgery:

One of the mainstays of plastic and reconstructive procedures is to ensure the patency and viability of grafting procedures. Hence, it is important to monitor and visualize the blood flow in diseased and reconstructed or grafted tissue, as well as their interface. The grafting procedures of interest involve those such as free tissue transfer procedures, which transfer skin, vessels, muscle, and bone from one part of the body to another. This procedure can be used, for example, after treating cancer or removing a tumor or after an accident or burn. The critical portion of a tissue transfer procedure is connecting the removed vessels to the vessels in the receiving site. Likewise, monitoring the patency and viability of an anastomosis of blood vessels is critical to the success of organ transplant or replantation procedures (e.g., a finger or other body part). The subject invention can be embodied to provide real-time or near-real-time blood flow information that assists surgeons in determining that the transferred vessels have proper blood flow and connection.

Ophthalmic Surgery:

Ophthalmic surgeries are often precise and increasingly conducted with robotic systems. For example, a number of surgeries (e.g., treatment of DR and ROP) involve irradiation of the retina with intense beams of laser to cauterize the vessels in the region to restrict undesired vascular proliferation. Such a laser systems could be augmented with speckle-based imaging systems that use a low-intensity laser in the invisible spectrum and generate blood flow information in the ROI. Such information might help the surgical system avoid certain vessels (e.g., major vessels) and confirm that flow in the vessels of interest is as desired (i.e., uninterrupted or stopped, as appropriate). The subject invention can be embodied to obtain and display real-time or near-real-time blood flow information to facilitate operating ophthalmic surgeons or surgical systems for decision making on navigation and outcomes.

Cardiac Surgery:

Many cardiac surgeries, including coronary artery bypass grafting, angioplasty, or endarterectomies require intraoperative evaluation of blood flow to ensure successful completion of the procedure. In such procedures, visual inspection with use of surgical loupes is a typical means of evaluating vessel patency. The subject invention can be embodied to provide real-time or near-real-time visualization of anatomical and physiological information in the FOV of the surgical loupes.

Endoscopic Surgery:

Endoscopic surgeries typically involve manipulation or resection of vessels, tissue, and organs. As with other surgical procedures, the ability to identify the vessel anatomy and physiology in the surgical site is critical for navigation to prevent unintended injury or rupture of the vessels and to identify areas of disease. For example, mesenteric ischemia (where blood flow to the gastrointestinal system is decreased due to blood vessel blockage), intraoperative, real-time or near-real-time monitoring of blood flow in the intestinal tissue can facilitate identification of specific regions of decreased flow to improve, for example, the efficiency of plaque removal procedures or to minimize the portion of damaged tissue that must be removed. Likewise, the ability to evaluate the patency and viability of vessels and organs following a resection is critical to the patient's outcome. In some cases these procedures are performed manually, semi-automatically, or automatically using a computer-aided surgical system. The subject invention can be embodied to provide real-time or near-real-time visualization of anatomical and physiological information during an endoscopic surgical procedure through the integration of LSCI with endoscopic instruments, with or without computer-aided surgical equipment.

In some embodiments, the system is designed as a stand-alone device for observing the target tissue in the surgical site. In some embodiments, the system is designed to operate in a modular fashion with a surgical microscope for observing the target tissue in the surgical site. In some embodiments, the system is designed to operate in conjunction with existing medical equipment, including electronic medical records; PACS, MRI, CT, and other imaging devices, laser ablation or electrocautery devices; or computer-aided surgical systems. In various embodiments, the system is designed to display the real-time or near-real-time blood flow images and other anatomical and physiological information in the viewfinder of a surgical microscope for observation by the surgeon during the surgical procedure. In some embodiments, the system is designed to display the real-time or near-real-time blood flow images and other anatomical and physiological information on a monitor in the surgical suite for observation by the surgeon and other members of the surgical team during the surgical procedure. In some embodiments, the display of the real-time or near-real-time blood flow images and other anatomical and physiological information is designed to overlay on another image (e.g., MRI or CT image of the preoperative anatomy, visual light image, or ICG angiogram) of the surgical site FOV. In some embodiments, the display is designed to present the real-time or near-real-time blood flow images and other anatomical and physiological information in one or more eyepieces of a surgical microscope.

In some embodiments, the system and method are designed for real-time or near-real-time blood flow imaging during non-surgical medical procedures to support clinical diagnosis or treatment decisions or for research purposes. In some embodiments, the system is designed to facilitate evaluation of physiological response to various stimuli, including visual stimuli, auditory stimuli, somatosensory stimuli, or motor stimuli. In some embodiments, the system is designed to facilitate evaluation of physical activity, including exercise, Valsalva maneuver, or physical therapy. In some embodiments, the system is designed to facilitate evaluation of pharmacological or other therapeutic agents or devices. In some embodiments, the system is designed for portable use in a clinical or community health environment.

In some embodiments, the system and method are designed for preclinical research in animal models or for veterinary applications. The subject invention can be embodied appropriately to meet the size and flow-related technical requirements of the specific animal tissue that is being imaged. For example, for imaging the rat brain, a FOV of 5 mm×5 mm may be adequate, and vessels of interest are likely to have diameters that are in the sub-millimeter range. Blood velocities and flow values are also different than in human vessels and, hence, the camera exposure time that is used for image acquisition may be different than in the clinical-grade system. In some embodiments for animal use, the working distance of the system's objective lens to the point of focus of the optical system may be shorter than in systems designed for clinical surgery. For example, in small animal research the exposed tissue is expected to be relatively shallow and, hence, the working distance of the system's objective lens to the point of focus of the optical system can be less than 60 mm and be variable to accommodate for the optical magnification of the system that may be desired for specific applications. Along with the relatively shorter working distance, the magnification and optical resolution for some embodiments for small animal use are higher. Application-specific requirements such as the diameter of the smallest vessel of interest in the target tissue, and the field of view of the target tissue may determine the optical magnification and the pixel resolution of the camera used. Various attributes of the system such as optical magnification, pixel size of the camera, size of the pixel array on the camera sensor, should be chosen such that the diameter of the smallest vessel of interest spans at least five pixels, and simultaneously, the active pixel area of the camera sensor images the entire field of view desired.

In some embodiments for animal use, the system is designed to emphasize modularity. In such embodiments, the system may comprise a stand to hold the various elements (e.g., illumination and camera modules) and allow for multiple degrees of freedom adjustment of the orientation to facilitate imaging of the ROI through various access-based or application-specific constraints of the preparation. In some embodiments, the system may comprise one or more mechanisms (e.g., a specialized platform or stereotaxic stand) for fixing, positioning, or securing the animal with respect to the system. In some embodiments, such mechanisms may be adjustable or modular for use in animals of different types and sizes. In some embodiments, the optical arrangement of the system can be adjusted to account for different applications and to accommodate various sizes of animals.

In various embodiments, the system and method are designed to compensate for motion artifact. Acquisition of multiple image frames makes LSCI susceptible to any motion artifacts. In such embodiments, the system is designed to reduce motion artifact by incorporating a stable surgical microscope or animal stand and rapid acquisition (less than 40 ms) of a small number of images (i.e., only 5 fast-acquired image frames in stLSCI) for every blood flow image generated. In some embodiments, the system comprises one or more motion compensation mechanisms (e.g., 3-axis accelerometer) to detect large or fast motion and a mechanism and method to tag any resulting speckle data as potentially inaccurate. In such embodiments, the system may comprise a mechanism to indicate to the user that the data is inaccurate, including through blanking of the display until the undesired motion ceases or the display of an appropriate message in the FOV. In some embodiments, the system employs a threshold for pixel intensity to eliminate noise from the displayed blood flow image.

In some embodiments, the one or more motion compensation mechanisms uses one or more or a combination of accelerometer and image data. In such embodiments, the system and method may involve the steps of and mechanism for feature detection (e.g., vessel detection using its ridge like appearance), followed by estimation of image registration parameters using an affine model with sub-pixel resolution. In some embodiments, accelerometer data may be used to bias the extraction of registration parameters through improved initialization of the motion compensation mechanism. For example, the registration parameters may be used to register sequentially acquired image frames to the first frame prior to the calculation of laser speckle contrast. In some embodiments, the system comprises a processor with sufficient speed and a storage module with sufficient memory to facilitate the computationally intensive process of real-time motion compensation (e.g., with real-time video mode, real-time vessel mode, or real-time relative mode). In some embodiments, the system is designed to facilitate motion compensation by acquiring image data in a snapshot mode. In some embodiments, a fiduciary marker may be added to the imaging target to serve as the feature for detection, motion identification, and compensation.

In some embodiments, the one or more motion compensation mechanisms uses information from other sensors (e.g., heart rate monitor, finger plethysmograph, respirator, or other surgical, anesthesiological, or medical equipment) to detect, calculate, or estimate motion artifact or to determine when and whether to indicate to the user that the data is inaccurate. In such embodiments, the system and method may involve the steps of and mechanism for feature detection from the information obtained from the other source (e.g., the peak or trough of a finger plethysmogram, which correspond to systole and diastole of a cardiac cycle, or the peak or trough of a respirator, which correspond to completion of inspiration and expiration, respectively), followed by estimation of image registration parameters or a decision regarding the need to inform the user of the potential inaccuracy of the data.

In some embodiments, the system and method are designed to compensate for glare and stray reflections.

The target tissue and surrounding surgical site may have exposed features that reflect light into the imaging optics towards the camera module, creating light artifacts (i.e., glare or stray reflections). Hence, in some embodiments, the system may comprise one or more mechanisms to detect such light artifacts and one or more mechanisms to indicate this potential inaccuracy to the user or compensate for this potential inaccuracy. One embodiment of a mechanism to detect the light artifact comprises an image-processing algorithm that identifies a cluster of saturating pixels that remains approximately constant through the sequentially acquired image frames. One embodiment of a mechanism to compensate for the potential inaccuracy due to the light artifact comprises selectively blanking out those pixels that are gathering erroneous data and displaying only those pixels that are gathering data without being affected by stray light.

In some embodiments, the system and method are designed to instruct to follow one or more steps to rectify the cause of motion artifact or stray light. For example, the user may be asked to change the relative position between the system and the imaging target or stabilize the image target and system with respect to each other.

BRIEF DESCRIPTION OF THE DRAWINGS

FIGS. 3A and 3B illustrate two embodiments of a system for real-time or near-real-time imaging of retinal blood flow.

DETAILED DESCRIPTION OF THE INVENTION

The following detailed description of the present subject matter refers to the accompanying drawings that show, by way of illustration, specific aspects and embodiments in which the present subject matter may be practiced. These embodiments are described in sufficient detail to enable those skilled in the art to practice the present subject matter. The invention can assume various embodiments that are suitable to its specific applications.

Figure 1:
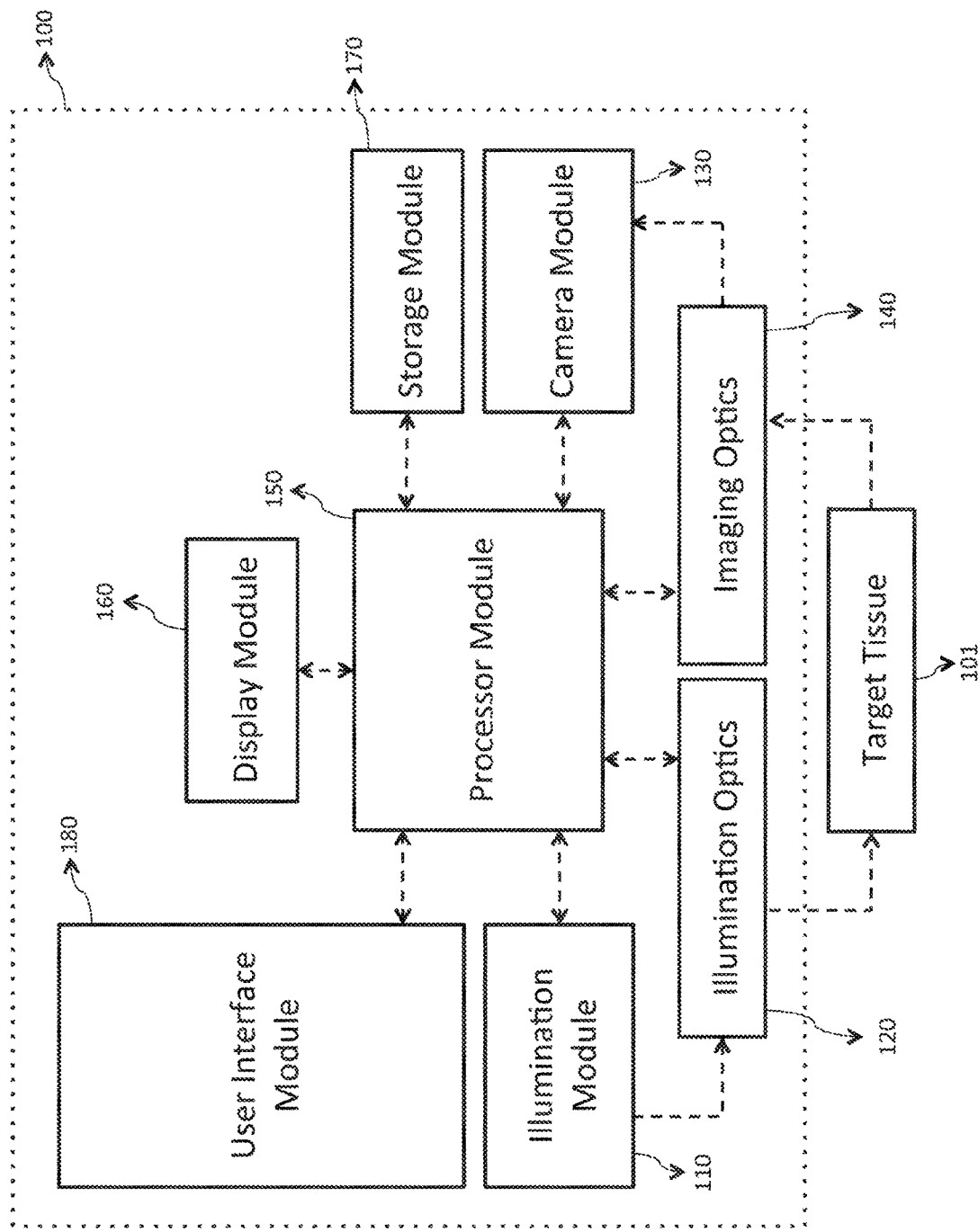
FIG. 1 is a block diagram illustrating an embodiment of a system for rapid examination of particulate flow in a target tissue.

FIG. 1 is a block diagram illustrating an embodiment of a system 100 for rapid examination of particulate flow in a target tissue 101. In various embodiments, the target tissue 101 comprises any tissue, organ, or organ system of any human or animal biological system, including but not limited to the cornea, sclera, retina, epidermis, dermis, hypodermis, skeletal muscle, smooth muscle, cardiac muscle, brain tissue, the spinal cord, the stomach, large and small intestines, pancreas, liver, gallbladder, kidneys, endocrine tissue, and associated or disassociated blood vessels and lymph vessels. In various embodiments, the system 100 comprises at least one illumination module 110 that is configured to generate at least one type of coherent light and to direct the generated light to the target tissue 101 being imaged; at least one illumination optics 120 that is configured such that the desired ROI is illuminated with the at least one type of coherent light; at least one camera module 130 that is configured to capture light that is reflected or scattered by the target tissue 101 being imaged; at least one imaging optics 140 that is configured such that the desired ROI is focused on the camera sensor within the camera module 130 with desired specifications of magnification, field of view, speckle size, spot size; at least one processor module 150 configured at least to estimate anatomical and physiological information in real-time or near-real-time using the data acquired by the camera module 130 and to control the operation of the system 100; at least one display module 160 configured to present the estimated anatomical and physiological information or equivalent parameters calculated from the image data by the processor module 150 or the raw data acquired by the camera module 130; at least one storage module 170 configured to store the estimated anatomical and physiological information or equivalent parameters calculated from the image data by the processor module 150 or the raw data acquired by the camera module 130 for temporary or future use; and at least one user interface module 180 configured to allow the user or operator to interact with the system 100 and program various options for features and parameters relevant to the performance of the various modules 110, 120, 130, 140, 150, 160, 170, 180 of the system 100.

The illumination module 110 comprises one or more light sources such that at least one of the sources produces coherent light (e.g., a laser) for speckle production and LSCI. In some embodiments, the illumination module 110 comprises additional light sources that produce coherent, non-coherent, or partially coherent light. The wavelength of the one or more lights being emitted by the light sources in the preferred embodiment lies in the 100-micron to 2000-micron range. In some embodiments, one or more wide-band light sources is used to produce light with more than one wavelength. In some embodiments, the one or more wide-band light sources is fitted with one or more filters to narrow the band for specific applications. Typically, non-coherent light sources are useful for reflectance- or absorption-based photography. In some embodiments, direct visualization and focusing of the system 100 on the target tissue 101 is achieved under non-coherent illumination. In some embodiments, the illumination module 110 incorporates mechanisms to control one or more of the power, intensity, irradiance, timing, or duration of illumination. Such a control mechanism may be electronic (examples include a timing circuit, an on/off switching circuit, a variable resistance circuit for dimming the intensity, or a capacitor-based circuit to provide a flash of light) or mechanical where one or more optical elements (examples include an aperture, a shutter, a filter, or the source itself) may be moved in or out of the path of illumination. In various embodiments, the light sources included in the illumination module 110 may be pulsatile or continuous, polarized or non-polarized.

The illumination optics 120 comprise an arrangement of one or more light manipulation components, which includes but is not limited to lenses, mirrors, apertures, filters, beam splitters, beam shapers, polarizers, wave retarders, and fiber optics, that serve the purpose of delivering light from the illumination module 110 to the desired ROI in the target tissue 101. The illumination optics 120 for the various embodiments includes components that manipulate the light in a manner than is useful for imaging the tissue of interest based on the specific application. In some embodiments, the illumination optics 120 includes a polarizer in the path of illumination that polarizes the light in a manner that significantly attenuates the light except when reflected or scattered by the target tissue 101.

The camera module 130 comprises at least one camera sensor or image acquisition device that is capable of transducing incident light to a digital representation (called image data). The camera module 130 is configured to direct the image data for further processing, display, or storage. In some embodiments, the camera module 130 comprises mechanisms that control image acquisition parameters, including exposure time (i.e., time for which the camera sensor pixel integrates photons prior to a readout), pixel sensitivity (i.e., gain of each pixel), binning (i.e., reading multiple pixels as if it was one compound pixel), active area (i.e., when the entire pixel array is not read out), among others. In the various embodiments, the at least one camera sensor used in the camera module 130 is a charge coupled device (CCD), complementary metal oxide semiconductor (CMOS), metal oxide semiconductor (MOS), based on photo-tubes, or another similar technology designed to capture image data.

The imaging optics 140 comprise an arrangement of one of more light manipulation components that serve the purpose of focusing the ROI of the target tissue 101 on to the at least one camera sensor of the camera module 130. In some embodiments, the imaging optics 140 comprise a means to form more than one image of ROI or sub-regions of the ROI of the target tissue 101. In some embodiments, the more than one image projects onto the one or more camera sensors or on the observer's retina through an eyepiece. In the various embodiments, the imaging optics 140 determine the imaging magnification, the field of view (FOV), size of the speckle (approximated by the diameter of the Airy disc pattern), and spot size at various locations within the FOV. In some embodiments, the imaging optics 140 includes light manipulation components that, in conjunction with components of the illumination optics 120, reduce the undesired glare resulting from various optical surfaces.

The processor module 150 comprises one or more processing elements configured to calculate, estimate, or determine, in real-time or near-real-time, one or more anatomical and physiological information or equivalent parameters calculated from the image data. The processor module 150 further comprises one or more processing elements configured to implement control functions for the system 100, including control of operation and configuration parameters of the camera module 130 (e.g., exposure time, gain, acquisition timing) and the illumination module 110 (e.g., timing, duration, and synchrony of illumination); control of the transmission of image data or derivatives thereof to the display module 160 or the storage module 170; control of which anatomical and physiological information or equivalent parameters should be calculated, estimated, or determined by the processor module 150; control of the position and orientation of one or more components of the illumination module 110, illumination optics 120, camera module 130, or imaging optics 140; and control of the power, safety criteria, operational procedures of the system 100.

In various embodiments, the processor module 150 is configured to calculate, estimate, or determine one or more anatomical and physiological information or equivalent parameters calculated from the image data in one or more of the following modes:

Real-time video mode—In the real-time video mode, the processor module 150 is configured to calculate, estimate, or determine one or more anatomical and physiological information or equivalent parameters calculated from the image data based on certain predetermined set of parameters and in synchrony or near-synchrony with the image acquisition. In the real-time video mode, the frame rate of the video presented by the display module 160 is greater than 16 frames per second (fps), allowing the surgeon to perceive uninterrupted video (based on the persistence of vision being $\frac{1}{16}^{th}$ of a second).

Real-time vessel mode—In real-time vessel mode, the system 100 is configured to allow the surgeon to select, using automatic or semi-automatic means, one or more vessels and to emphasize the anatomical and physiological information in the selected vessels over other vessels in the FOV. In some embodiments, the system 100 is configured to allow the surgeon to select all arteries or all veins, extracted automatically, in the entire FOV or an ROI of the FOV. In such embodiments, the extraction may be achieved by either (a) computing the anatomical or physiological information in the entire field but displaying only the anatomical or physiological information in the selected vessels, or (b) computing the anatomical or physiological information only in the selected vessels and displaying the anatomical or physiological information accordingly, or (c) computing the anatomical or physiological information in the entire field and enhancing the display of the selected vessels through an alternate color scheme or by highlighting the pre-selected vessels centerlines or edges.

Real-time relative mode—In the real-time relative mode, the processor module 150 includes the baseline values of anatomical and physiological information in its computation of instantaneous values of anatomical or physiological information. The real-time relative mode may be implemented as a difference of instantaneous values of anatomical or physiological information from the baseline values, or as a ratio of the anatomical or physiological information with respect to baseline values.

Snapshot mode—In the snapshot mode, the processor module 150 generates a single image of the anatomical or physiological information in the surgical FOV. In this embodiment, the processor module 150 may utilize a greater number of frames for computing the anatomical or physiological information than it utilizes during the real-time modes, since the temporal constraints are somewhat relaxed. In the snapshot mode, all the functionalities of the real-time modes are also possible (e.g., display of change of blood flow instead of blood flow, or enhanced display of a set of selected vessels).

The display module 160 comprises one or more display screens configured to present the estimated anatomical and physiological information or equivalent parameters calculated from the image data by the processor module 150 or the raw data acquired by the camera module 130. In some embodiments, the one or more display screens are physically located in close proximity to the remaining elements of the system 100. In some embodiments, the one or more display screens are physically located remotely from the remaining elements of the system 100. In the various embodiments, the one or more display screens are connected by wired or wireless means to the processor module 150. In some embodiments, the display module 160 is configured to provide the observer with a visualization of the ROI and the estimated anatomical and physiological information or equivalent parameters calculated from the image data by the processor module 150. In the various embodiments, the display module 160 is configured for real-time visualization, near-real-time visualization, or retrospective visualization of imaged data or estimated anatomical and physiological information or equivalent parameters calculated from the image data that is stored in the storage module 170. Various aspects of anatomical and physiological information, or equivalent parameters and other outputs of the processor may be presented in the form of monochrome, color, or pseudo-color images, videos, graphs, plots, or alphanumeric values.

The storage module 170 comprises one or more mechanisms for archiving electronic data, including the estimated anatomical and physiological information or equivalent parameters calculated from the image data by the processor module 150 or the raw data acquired by the camera module 130. In various embodiments, the storage module 170 is configured to store data for temporary and long-term use. In various embodiments, the one or more mechanisms includes random access memory (RAM) units, flash-based memory units, magnetic disks, optical media, flash disks, memory cards, or external server or system of servers (e.g., a cloud-based system) that may be accessed through wired or wireless means. The storage module 170 can be configured to store data based on a variety of user options, including storing all or part of the estimated anatomical and physiological information or equivalent parameters calculated from the image data by the processor module 150 or the raw data acquired by the camera module 130.

The user interface module 180 comprises one or more user input mechanisms to permit the user to control the operation and preferred settings of the various modules 110, 120, 130, 140, 150, 160, 170, 180 of the system 100. In various embodiments, the one or more user input module includes a touch-screen, keyboard, mouse or an equivalent navigation and selection device, and virtual or electronic switches controlled by hand, foot, eye, or voice. In some embodiments, the one or more user input mechanisms is the same as the one or more display screens of the display module 160.

In some embodiments, the user interface module 180 is customized for two types of users. The primary user of the system 100 is one or more surgeons performing the surgery. In some embodiments, the system 100 is configured to facilitate performing the surgery via computer-aided surgical systems. The anatomical and physiological information provided to the one or more surgeons to assist with decision-making during the surgical operation at various times. The user interface module 180 of the system 100 allows the user to:

Turn on/off (or standby) the visualization of anatomical or physiological from surgical microscope FOV as desired (referred to as the "real-time video mode"), which is achievable using a variety of triggers, including the pressing of a physical or virtual button or similar switch by the surgeon's hand, finger or foot, the creation of an audible trigger, or the motion of an object or body part;

Acquire and visualize accurate and real-time anatomical or physiological information in a blood vessel of interest (referred to as the "real-time vessel mode"), which is implemented by the system 100 either on a continuous basis, or when triggered by the surgeon using a variety of triggers, including the pressing of a physical or virtual button or similar switch by the surgeon's hand, finger or foot, the creation of an audible trigger, or the motion of an object or body part;

Visualize either the instantaneous estimation of anatomical or physiological information or the change in measurement of anatomical or physiological information (referred to as the "real-time relative mode") from a preset baseline value, which are both implemented by the system 100 through appropriately storing baseline values in the storage module 170 and configuring the processor module 150 to either not utilize or utilize the baseline values in its computation of instantaneous values of the anatomical or physiological information to obtain the anatomical or physiological information or change in the anatomical or physiological information.

Store snapshots or videos of the anatomical or physiological information in the surgical field if needed (referred to as the "snapshot mode"), which is implemented by the system 100 by providing the user a "capture" button (physical or virtual), and subsequently handled by the processor module 150, which directs the data to the storage module 170.

The secondary user of the system is the assisting staff of the operation, potentially including scrub nurse, assisting nurse practitioner, anesthesiologist, and other clinicians in the operating room or positioned remotely outside the operating room during the operation. The user interface module 180 of the system 100 allows the secondary user to assist the surgeon to set up the system, modify parameters, and perform certain functions in real-time that the primary user may require (capture image, save video, etc.), some or all of which may be enabled by a portion of the user interface module 180 that is customized for secondary access. Thus, in some embodiments, the user interface module 180 comprises two sub-modules, a first sub-module that will be accessible to the operating surgeon and a second sub-module that will be accessible by the secondary user.

Figure 2B:
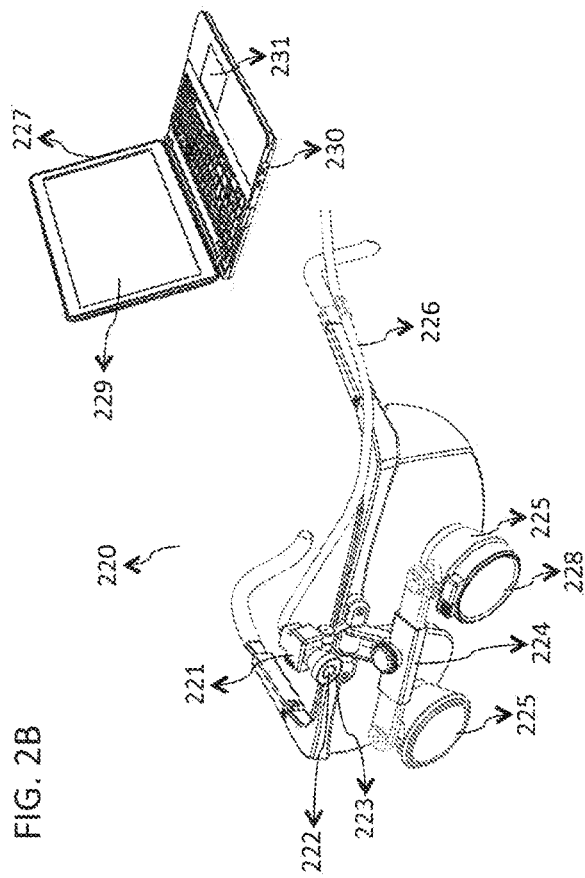
FIGS. 2A, 2B, and 2C illustrate different embodiments of a system designed for real-time estimation and visualization of blood flow during surgery.
Figure 2C:
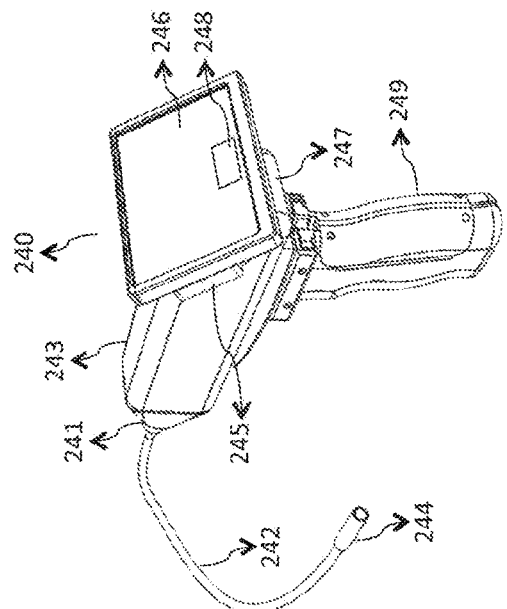
Figure 2A:
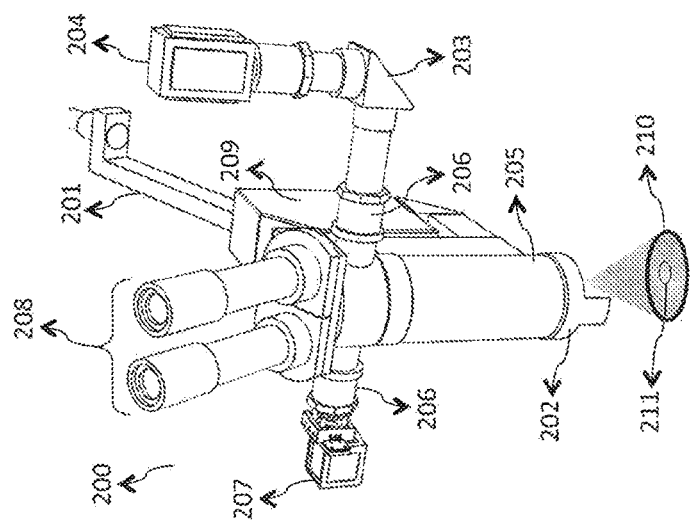

FIGS. 2A, 2B, and 2C illustrate different embodiments of a system designed for real-time estimation and visualization of blood flow during surgery. The embodiment in FIG. 2A shows a system 200 that includes a physically-integrated surgical microscope 201. The illumination optics and imaging optics leverage the optical assembly 205 of the surgical microscope 201. The system 200 estimates blood flow within an FOV 210 the size of which is determined by the magnification settings of the surgical microscope 201. The system 200 estimates the blood flow within the depth of focus as set by the surgical microscope 201. When used in human surgical environments, the FOV 210 has a diameter that ranges from approximately 10 mm to 50 mm in diameter. When used in veterinary environments, the FOV 210 has a diameter that ranges from approximately 5 mm to 50 mm in diameter.

In FIG. 2A, the system 200 utilizes multiple optical ports 206 to engage 1) the imaging optics 203 to form an image of the FOV 210 on the camera sensor of the camera module 204, and 2) the display module 207 to project the anatomical and physiological information in one or more of the eyepieces 208 of the surgical microscope 201. In some embodiments, an aperture is included in the imaging optics 203 that determines the diameter of the Airy disc (i.e., speckle size) for a given magnification and the wavelength of the laser used. The system 200 employs an illumination module 202 with laser diode of light in the invisible range (700 nm to 1000 nm) to prevent disruption of the surgical field, a uniform beam shaper to achieve uniform top-hat or flat-top illumination that transforms a Gaussian beam of the laser diode into a uniform intensity distribution, and a near-infrared (NIR) polarizer to generate a linearly polarized illumination. In some embodiments, laser diode homogenization and reshaping may be assisted by two orthogonal Powell lenses. In some embodiments, one or more fiber-optic illumination ports may be employed to transmit light to the surgical area to illuminate the ROI 211. In some embodiments, the wavelength of coherent light is selectively matched to fluorescent dyes to combine LSCI with other imaging techniques (e.g., ICG angiography).

The camera module 204 includes a CMOS camera sensor that comprises a 2048×2048 pixel array, each of which is 5.5 μm×5.5 μm in size such that the imaging optics 203 forms an image of the entire FOV 210 on the camera sensor of the camera module 204. In various embodiments, the pixels of the camera sensor may be binned at the hardware level or software level such that the data is read out in a manner that each frame contains 1024×1024, 512×512, or 256×256 pixel array (corresponding to 2×2, 4×4, or 8×8 binning, respectively). In some embodiments, data acquired by the camera module 204 is directed to an FPGA 209 via a camera link at a rate greater than or equal to 120 frames per second. In some embodiments, the FPGA performs stLSCI calculations and generates 24-bit RGB color representations of blood flow information for presentation to the user via the display module 207 over an HDMI interface.

FIG. 2B shows an illustration of a system 220 designed for use with surgical or dental loupes. The system 220 comprises an illumination module 221 that is configured to generate coherent light in the invisible range (700 nm to 1000 nm) and non-coherent light in the visible range (400 nm to 700 nm) directed to the target tissue being imaged; illumination optics 222 that is configured such that the desired ROI is illuminated with the coherent light and illumination optics 223 that is configured such that the desired ROI is illuminated with the non-coherent light; a camera module 224 that is configured to capture light that is reflected or scattered by the target tissue being imaged; imaging optics 225 that is configured such that the desired ROI is focused on the camera sensor within the camera module 224 with desired specifications of magnification, field of view, speckle size, spot size; a cable 226 for facilitating data transmission between the camera module 224, the illumination module 221, and the processor module 227, which is configured to estimate anatomical and physiological information in real-time or near-real-time using the data acquired by the camera module 224 and to control the operation of the system 220; two display modules 228 and 229 configured to present the estimated anatomical and physiological information or equivalent parameters calculated from the image data by the processor module 227 or the raw data acquired by the camera module 224; a storage module 230 configured to store the estimated anatomical and physiological information or equivalent parameters calculated from the image data by the processor module 227 or the raw data acquired by the camera module 224 for future use; and a user interface module 231 configured to allow the user or operator to interact with the system 220 and program various options for features and parameters relevant to the performance of the various modules 221, 222, 223, 224, 225, 226, 227, 228, 229, 230 of the system 220.

FIG. 2C shows an illustration of a system 240 designed for use in an endoscopic surgical setting. The system 240 comprises an illumination module 241 that is configured to generate coherent light in the invisible range (700 nm to 1000 nm) and non-coherent light in the visible range (400 nm to 700 nm) directed to the target tissue being imaged; illumination optics 242 that employs one or more fiber optics such that the desired ROI is illuminated with the coherent light and non-coherent light; a camera module 243 that is configured to capture light that is reflected or scattered by the target tissue being imaged; imaging optics 244 that is configured such that the desired ROI is focused on the camera sensor within the camera module 243 with desired specifications of magnification, field of view, speckle size, spot size; a processor module 245 that is configured to estimate anatomical and physiological information in real-time or near-real-time using the data acquired by the camera module 243 and to control the operation of the system 240; a display module 246 configured to present the estimated anatomical and physiological information or equivalent parameters calculated from the image data by the processor module 245 or the raw data acquired by the camera module 243; a storage module 247 configured to store the estimated anatomical and physiological information or equivalent parameters calculated from the image data by the processor module 245 or the raw data acquired by the camera module 243 for future use; and a user interface module 248 configured to allow the user or operator to interact with the system 240 and program various options for features and parameters relevant to the performance of the various modules 241, 242, 243, 244, 245, 246, 247 of the system 240. The system 240 comprises a handle 249 to facilitate handheld use during surgery.

FIGS. 3A and 3B illustrate two embodiments of a system for real-time or near-real-time imaging of retinal blood flow. In the embodiment illustrated in FIG. 3A, the system 300 is designed for clinical use for research or diagnostic purposes. The system 300 comprises a retinal imaging device 301 that houses an illumination module configured to generate coherent light in the visible or invisible range (400 nm to 1500 nm) and non-coherent light in the visible range (400 nm to 700 nm) directed to the desired ROI of the retina; illumination optics that is configured such that the desired ROI of the retina is illuminated with the coherent light and non-coherent light; a camera module that is configured to capture light that is reflected or scattered by the illuminated ROI of the retina; imaging optics that is configured such that the desired ROI of the retina is focused on the camera sensor within the camera module with desired specifications of magnification, field of view, speckle size, spot size. The retinal imaging device 301 is designed to fit onto a bench-top stand 302 that allows the user to manipulate the position and orientation (i.e., height, angle, and proximity) of the device to the retina of the subject 303 being imaged. A chin rest 304 is used to reduce motion of the subject's 303 head and to fix the relative distance between the subject's 303 retina and the retinal imaging device 301. The system 300 further comprises a laptop computer 305 that houses a processor module configured to estimate anatomical and physiological information in real-time or near-real-time using the data acquired by the camera module and to control the operation of the retinal imaging device 301; a display module configured to present the estimated anatomical and physiological information or equivalent parameters calculated from the image data by the processor module or the raw data acquired by the camera module of the retinal imaging device 301; a storage module configured to store the estimated anatomical and physiological information or equivalent parameters calculated from the image data by the processor module or the raw data acquired by the camera module for future use; and a user interface module configured to allow the user or operator to interact with the retinal imaging device 300 and program various options for features and parameters relevant to the performance of the various modules of the system 300. The retinal imaging device further comprises a display module 306 configured to present the estimated anatomical and physiological information or equivalent parameters calculated from the image data by the processor module or the raw data acquired by the camera module.

In FIG. 3B, the system 320 is implemented as a retinal imaging device 321 designed for handheld use. The retinal imaging device 321 houses an illumination module comprising of a diode laser (e.g., a 650 nm red laser) and a visible wavelength LED source (e.g., an LED with peak emission wavelength of 540 nm); a camera module comprising of a CMOS camera; display module 322 comprising of an LCD screen; a storage module comprising of an SD card module; a processor module comprising of an Arduino-based microcontroller or an FPGA. The user interface module is implemented through a combination of switches on the device or on a remote controller, one or more on-screen menus on the display module 322, and a keyboard and mouse for parameter and information entry. The retinal imaging device 321 employs a rubber eye cup 323 to stabilize the device with respect to the eye of the subject 324. In some embodiments, the retinal imaging device 321 includes a wireless module that facilitates transmission of electronic data to a local laptop computer or mobile computing device or to a remote server or server system. In some embodiments, the system 320 employs a laptop computer or mobile computing device as a secondary display module. In some embodiments, the system 320 includes a transmission module that facilitates transmission of electronic data to a remote server or server system for further storage, processing, or display. In some embodiments, the system 320 comprises a processing module configured to display anatomical and physiological information from retinal vasculature with a latency of less of than 100 milliseconds.

Figure 4:
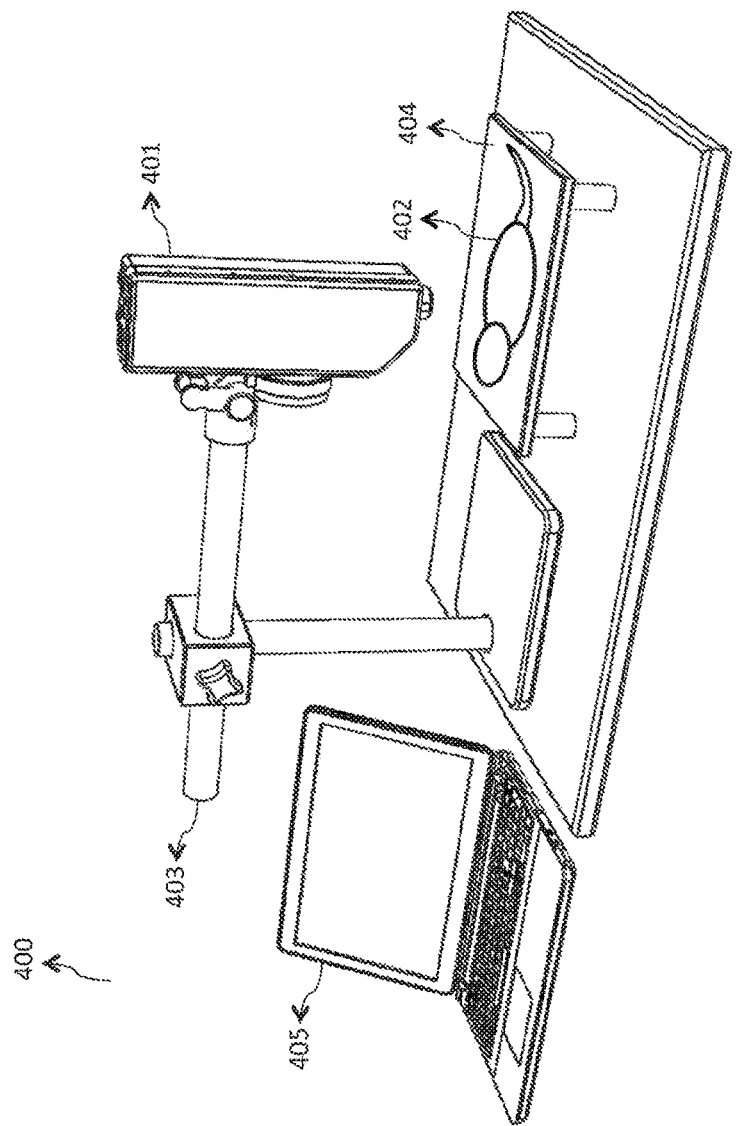
FIG. 4 illustrates an embodiment of a system for imaging in anesthetized and restrained animals.

FIG. 4 illustrates an embodiment of a system for imaging in anesthetized and restrained animals. The system 400 comprises an imaging device 401 that houses an illumination module configured to generate at least one coherent light in the visible or invisible range (400 nm to 1500 nm) and at least one non-coherent light in the visible range (400 nm to 700 nm) directed to the target tissue of an anesthetized and restrained animal 402; illumination optics that is configured such that the target tissue is illuminated with the coherent light and non-coherent light; a camera module that is configured to capture light that is reflected or scattered by the illuminated ROI of the target tissue; imaging optics that is configured such that the desired ROI of the target tissue is focused on the camera sensor within the camera module with desired specifications of magnification, field of view, speckle size, spot size. The imaging device 401 is designed to fit onto a bench-top stand 403 that allows the user to manipulate the position and orientation (i.e., height, angle, and proximity) of the device relative to the animal 402 being imaged. The system further comprises a platform 404 (e.g., a stereotaxic frame) used to reduce motion of target tissue of the animal 402 and to fix the relative distance between the target tissue of the animal 402 and the imaging device 401. The system 400 further comprises a laptop computer 405 that houses a processor module configured to estimate anatomical and physiological information in real-time or near-real-time using the data acquired by the camera module and to control the operation of the imaging device 401; a display module configured to present the estimated anatomical and physiological information or equivalent parameters calculated from the image data by the processor module or the raw data acquired by the camera module of the imaging device 401; a storage module configured to store the estimated anatomical and physiological information or equivalent parameters calculated from the image data by the processor module or the raw data acquired by the camera module for future use; and a user interface module configured to allow the user or operator to interact with the imaging device 401 and program various options for features and parameters relevant to the performance of the various modules of the system 400. In some embodiments, the system 400 includes a transmission module that facilitates transmission of electronic data to a remote server or server system for further storage, processing, or display. In some embodiments, the imaging device 401 is designed specifically for imaging of surface or subcutaneous vasculature. In some embodiments, the imaging device 401 is designed specifically for imaging of the vasculature of surgically exposed tissue. In some embodiments, the imaging device 401 is designed specifically for imaging of retinal vasculature. In some embodiments, specific parts (e.g., optical elements) of the imaging device 401 may be exchanged with other parts to optimize the system 400 for imaging the vasculature of specific tissue.

Figure 5:
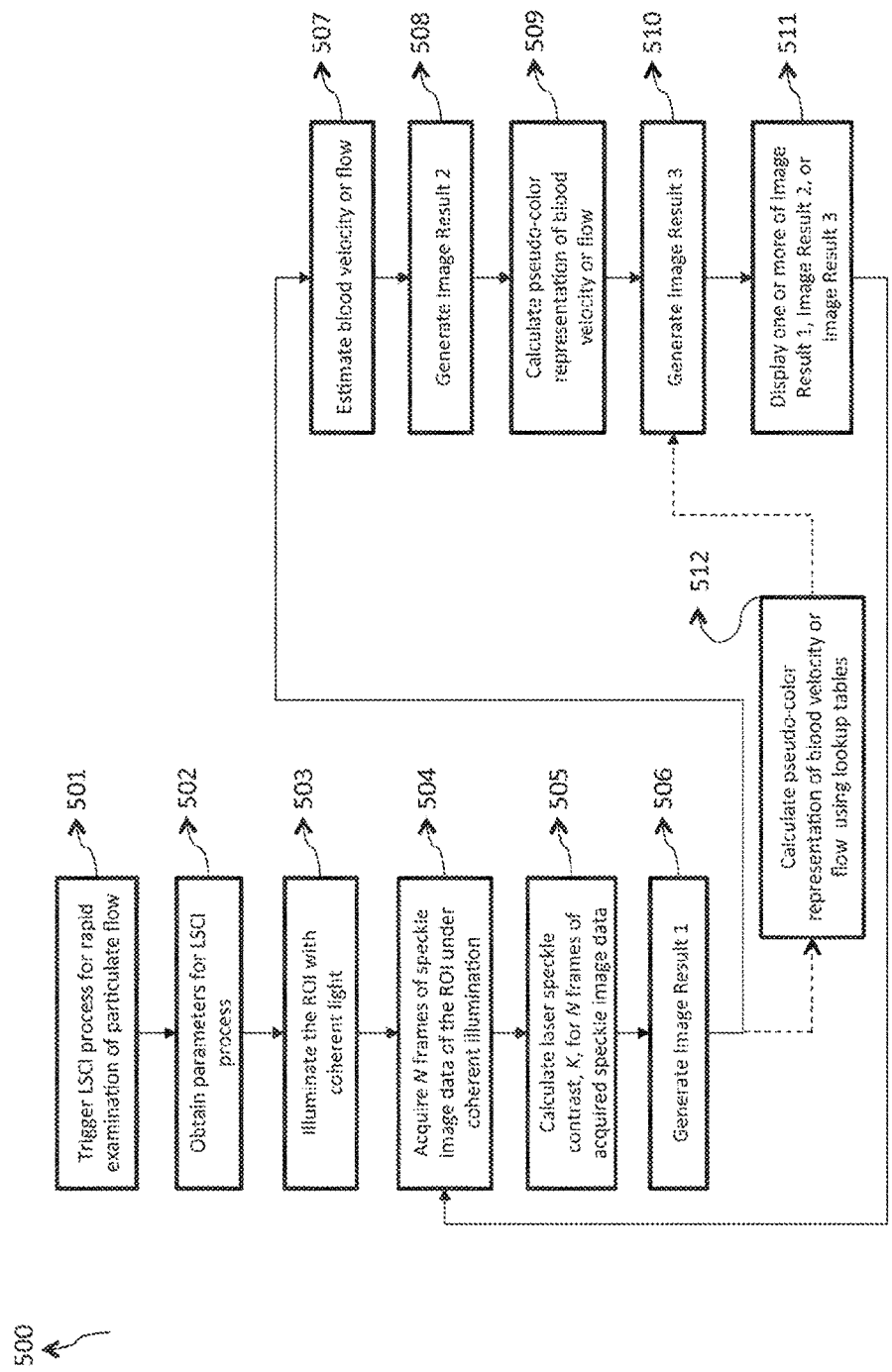
FIG. 5 is a flowchart depicting an embodiment of a method for rapid examination of particulate flow using LSCI.

FIG. 5 is a flowchart depicting an embodiment of a method for rapid examination of particulate flow using LSCI. In this embodiment, the LSCI process 500 for rapid examination of particulate flow begins once triggered 501. In various embodiments, the trigger 501 that starts the LSCI process 500 can be manual (i.e., user-generated), automated (i.e., system-generated), or semi-automated (i.e., user- or system-generated). Once the triggering step 501 has commenced, the system that implements the LSCI process 500 obtains the necessary parameters, including exposure time, frame rate, resolution, binning factor, and gain. The various parameters can be provided by either the user or obtained from memory. Parameters may be modified manually or automatically using feedback from the imaging result and quality of one or more electronic data. The system then, at 503, illuminates the ROI of the target tissue with coherent light and acquires, at 504, a stack of N frames under this coherent light illumination at the predetermined exposure time and gain. Next, the system calculates, at 505, speckle contrast, K, for the pixels of interest in the field of view, using the N frames of acquired speckle image data, generating an LSCI image (Image Result 1) at 506. From the LSCI image the system estimates, at 507, blood velocity or flow, generating Image Result 2 at 508. At 509, the system converts Image Result 2 to a pseudo-color representation of blood velocity or flow (Image Result 3), providing for intuitive visualization of blood velocity or flow information. The system displays, at 511, Image Result 1, Image Result 2, or Image Result 3, as appropriate, depending on the user-selected or preset display setting. Based on the parameter settings at 502, the LSCI process 500 continues to provide rapid examination of particulate flow. An embodiment may generate Image Result 3 directly from Image Result 1, at 512, using pre-determined lookup tables that assign color-codes directly to speckle contrast values.

Figure 6:
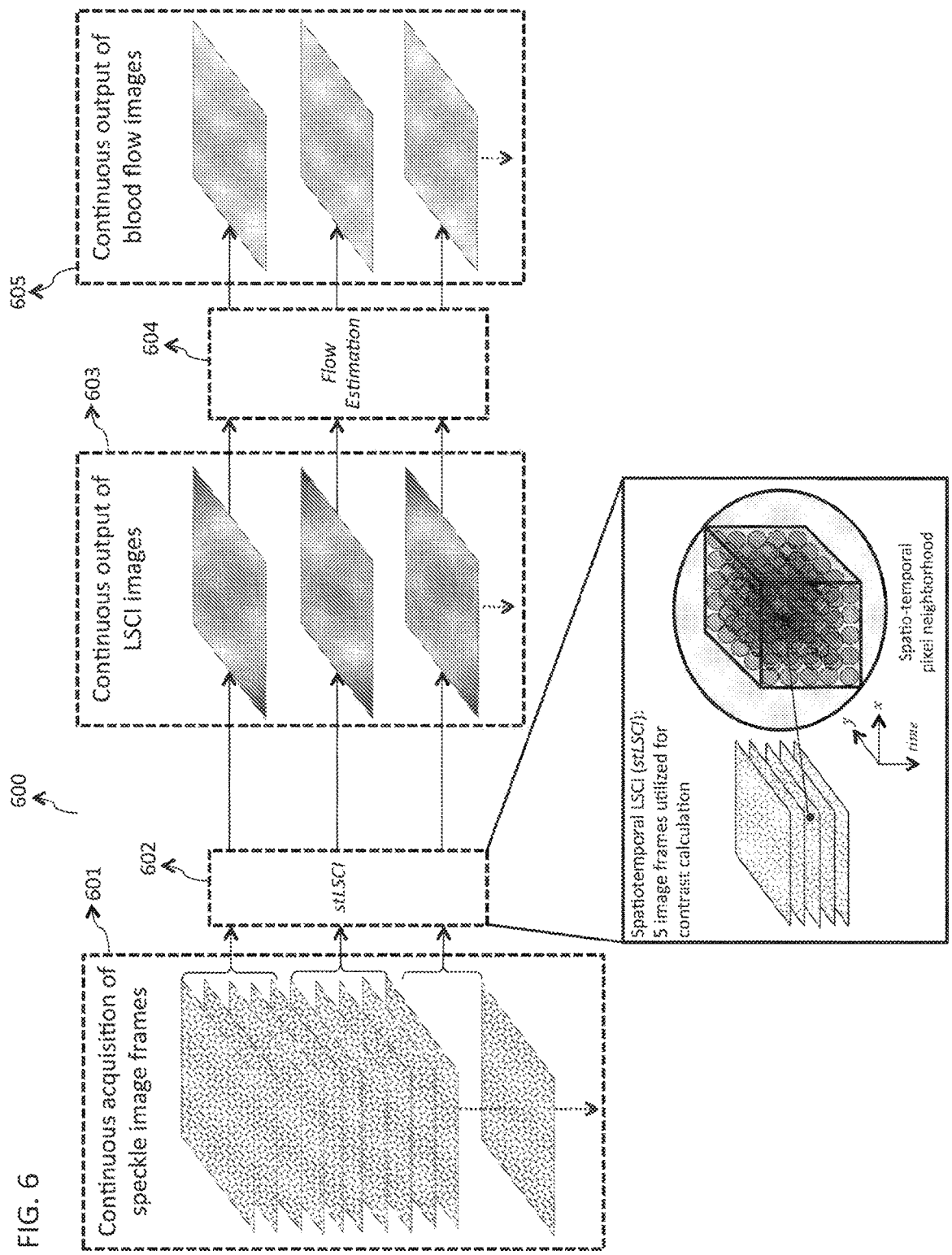
FIG. 6 illustrates an embodiment of a spatiotemporal method of calculating laser speckle contrast for rapid examination of particulate flow in a target tissue.

FIG. 6 illustrates an embodiment of a spatiotemporal method of calculating laser speckle contrast for rapid examination of particulate flow in a target tissue. The method 600 is intended to provide real-time or near-real-time acquisition, processing, and display of blood flow information from the vasculature of any tissue. The method 600 begins with the acquisition, at 601, of speckle image frames of the vasculature under coherent light illumination. In this embodiment, a stack of N=5 speckle image frames are acquired at 601. In other embodiments, the stack of speckle image frames acquired at 601 ranges from 2 to 21 (larger number of frames may be enabled by cameras with ultrafast image acquisition). The stack of speckle image frames acquired at 601 are transferred and processed at 602 using stLSCI to calculate the laser speckle contrast values and generate an LSCI image at 603. The LSCI image is processed at 604 to estimate the blood flow in the vasculature within the FOV of the speckle image frames acquired at 601. In some embodiments, the flow estimation at 604 involves integration of blood velocities across the cross-section of the vessel to provide cumulative flow in one or more vessels at one or more cross-sections; while in some embodiments, only blood velocity may be estimated and interpreted as the localized blood flow at the underlying pixel. Some embodiments may implement both methods of flow estimation, and permit the user to select a desired method. The flow estimation at 604 generates a blood flow image for visualization by a user or further processing. The method 600 continuously repeats as additional speckle image frames are acquired at 601. In various embodiments, the stack of speckle image frames acquired at 601 used to generate each subsequent LSCI image at 603 and the corresponding blood flow image at 605 includes 0 to N−1 of the speckle image frames in the previous stack, where n is the number of speckle image frames acquired at 601 to produce the LSCI image at 603 and the corresponding blood flow image at 605. By rapid visualization of new blood flow images at 605, the method 600 is able to achieve a real-time or near-real-time display of blood flow information from the vasculature of the imaged tissue.

Figure 7:
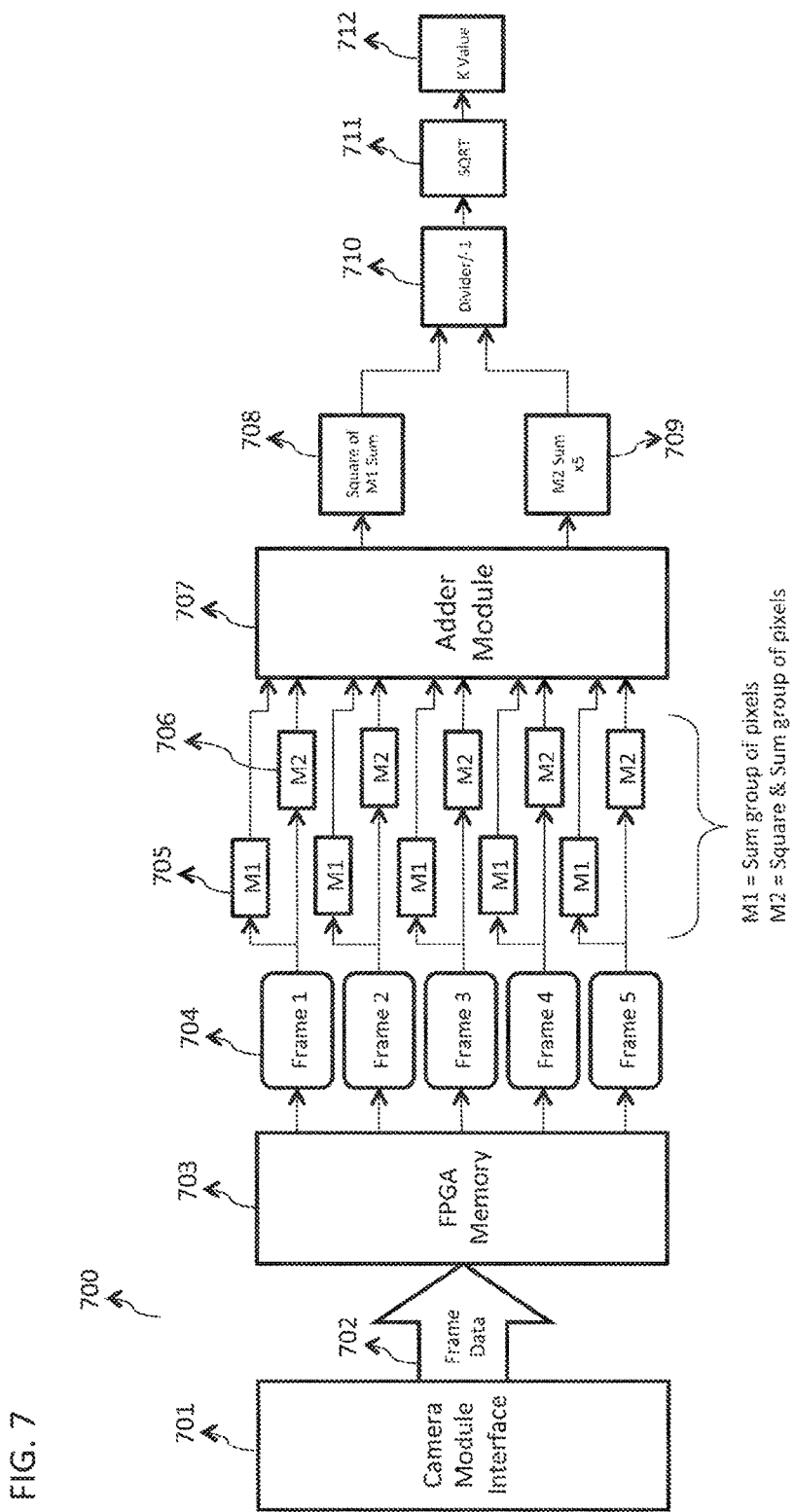
FIG. 7 illustrates a method for performing LSCI on a field programmable gate array.

FIG. 7 illustrates a method for performing LSCI on a field programmable gate array. In this embodiment, the method 700 begins with the acquisition of a stack of speckle image frames, which are transferred at 702 via an FPGA camera module interface at 701. The FPGA utilizes a finite number of memory and temporary registers to compute laser speckle contrast images according to the spatio-temporal processing scheme. In some embodiments, the FPGA receives 1024×1024 pixel data and stores it into the FPGA's Direct Memory (FPGADM) 703. The frames continue to refresh until the method 700 is halted. In this embodiment, at 704 the first 5 frames are copied from the FPGADM and stored in a different temporary location within the FPGADM. The processing on these 5 frames begins at 705 and, in parallel, the next 5 frames arrive at the frame rate of the camera and are similarly stored on the FPGADM at 703. Acquiring pixels at 82 MHz with four pixels per clock requires about 4 ms to store a 1024×1024 frame, allowing 20 ms to complete all processing on the 5 frames before the next 5 frames are ready for processing. Starting from the bottom right corner, 25 pixels (equivalent to a 5×5 pixel spatial window) at a time are read from each copied frame, padding the edge cases with zeros. The group of pixels are sent to two memory modules per frame in parallel. The first memory module (M1), at 705, maintains a sum of the pixel values while the second memory module (M2), at 706, maintains a sum of the square of pixel values. Both the modules at 705 and 706 store the sums of the first column of 5 pixels and subtract it from the total for the next pixel in the current line, allowing the FPGA to read only 5 pixels for the rest of the outputs for the current line instead of 25. The outputs of all the M1 modules are added at 707 and then squared at 708 to form an output (Sum_Sq) while the outputs of all the M2 modules are summed at 707 to form an output (Sq_Sum). Next, Sq_Sum is shifted bitwise to the left by two and then summed with Sq_Sum (equivalent to multiplying by 5) at 709. This result is, at 710, divided by Sum_Sq and reduced by 1 to produce the final sum of the group of pixels across the 5 frames. At 711, the square root of this final sum produces the K value, at 712, for the pixel. The method 700 repeats for each line in the frames and then for the next set of five frames. In some embodiments, where the 20 ms time requirement cannot be met, another set of modules is added that starts from the top right corner of the frame.

Once the K value is computed for a pixel, the value of $1/\tau_c$ is obtained for the pixel using look-up tables stored in the memory of the FPGA. This value of $1/\tau_c$ indicates the amount of perfusion at the pixel. Each values of $1/\tau_c$ has a unique representation in pseudocolor (in the red-green-blue of RGB space). Thus, each matrix of $1/\tau_c$ values is transformed using look-up tables to three matrices, one each for the red, green, and blue components of the pseudocolor representation of the entire ROI. As described, the computation of $1/\tau_c$ as an intermediate step may be unnecessary, and the RGB matrices may be computed directly from the K values using look-up tables. In addition, the FPGA also adds a finite time-latency to the stream of raw images acquired from the camera module, and creates a linear combination of the raw image and each of the RGB matrices. When the latency is matched with the amount of time required for the FPGA to generate the first set of RBG matrices measured from the onset of image acquisition, this processing scheme creates a stream of compound images wherein the blood flow information is depicted in pseudo-color and overlaid on the raw image of the target ROI. This stream of compound images that lag the input by a specific latency constitute the output in this embodiment.

The FPGA then directs the output (values of $1/\tau_c$) as a 24-bit RGB color representation to the display module. In this embodiment, the display module comprises an LCD screen that displays the stream of compound images in real-time or near-real-time, as determined by the latency introduced during the generation of the output image stream. The LCD screen includes a driver module that parses the streaming image data and displays it on an appropriately sized screen.

What is claimed is:

1. A vascular imaging system, comprising:
    at least a first light source configured to generate at least first coherent light to illuminate a target tissue;
    an image acquisition device configured to capture light that is reflected or scattered by the target tissue;
    a first optical assembly configured to direct the first coherent light to a region of interest of the target tissue;
    a second optical assembly configured to direct the reflected or scattered light from the region of interest of the target tissue to the image acquisition device; and
    one or more processors configured to:
        calculate laser speckle contrast values at any pixel in any acquired image frame using data from the said pixel and the said pixel's adjacent spatial and temporal neighborhood comprising one or more additional pixels in the same said any acquired frame and corresponding pixels from a predetermined number of adjacent previously acquired frames, wherein data from said any acquired image frame is also used to calculate second laser speckle contrast values for at least one subsequently acquired image frame.

2. The vascular imaging system of claim 1, wherein the first coherent light has a wavelength in the invisible infrared or near infrared spectrum.

3. The vascular imaging system of claim 1, further comprising:
    a second light source configured to generate first non-coherent light to illuminate the target tissue.

4. The vascular imaging system of claim 1, wherein the target tissue comprises one or more of a cornea, sclera, retina, epidermis, dermis, hypodermis, skeletal muscle, smooth muscle, cardiac muscle, cerebrovascular tissue, stomach, large or small intestines, pancreas, liver, gallbladder, kidneys, or lymphatic tissue of a human or animal.

5. The vascular imaging system of claim 1, further comprising:
a display module configured to present electronic data generated by the one or more processors; and
one or more interface modules configured to allow a user to interact with the electronic data;
wherein the electronic data comprises image data captured by the image acquisition device, anatomical or physiological information calculated from the image data, and/or patient-specific data acquired from one or more other sources including one or more of electronic health records, electronic medical records, personal health records, picture archiving and communications systems, heart rate monitor, finger plethysmograph, respirator, or other surgical, anesthesiological, or medical equipment.

6. The vascular imaging system of claim 5, wherein the vascular imaging system is further configured to perform angiography, wherein said angiography comprises one or more of fluorescein angiography, indocyanine green angiography, or angiography using an appropriate contrast agent or dye.

7. The vascular imaging system of claim 1, further comprising:
a display module configured to present an overlaid visualization of electronic data generated by the one or more processors on a view of the target tissue or directly on the target tissue.

8. The vascular imaging system of claim 1, wherein the one or more processors are configured to compensate for motion artifact.

9. The vascular imaging system of claim 1, wherein the vascular imaging system is configured for performing real-time or near real-time laser speckle contrast imaging during surgical procedures.

10. The vascular imaging system of claim 1, wherein one or more components of the vascular imaging system are configured for portability, wherein said portability includes handheld, head-mounted, or other wearable use or integration into a movable trolley-type system.

11. The vascular imaging system of claim 1, wherein one or more components of the vascular imaging system are configured for endoscopic imaging.

12. The vascular imaging system of claim 1, wherein one or more components of the vascular imaging system are configured for intravascular imaging.

13. The vascular imaging system of claim 1, wherein the vascular imaging system interacts with other sensory, therapeutic, or disease management systems to generate at least one actionable output.

14. The vascular imaging system of claim 1, wherein:
the one or more processors are further configured to calculate one or more of anatomical information or physiological information of a vessel; and
the vessel is one or more of a naturally occurring or artificial blood vessel.

15. The vascular imaging system of claim 14, wherein the artificial blood vessel includes a tube through which blood flows or can be directed to flow.

16. The vascular imaging system of claim 1, wherein the one or more processors are configured to calculate a square of a laser speckle contrast value for a certain pixel in a certain image frame by:
calculating a sum of one or more pixel intensities that have a pre-determined spatial or temporal relationship with said certain pixel;
calculating a sum of squares of the one or more pixel intensities;
maintaining a first memory location within which said calculated sum of the one or more pixel intensities is stored;
maintaining a second memory location within which said calculated sum of squares of the one or more pixel intensities is stored; and
calculating the square of the laser speckle contrast value by subtracting one from the result of dividing the product of a value in the second memory location and a number of frames from which the one or more pixel intensities are selected by a square of the value in the first memory location.

17. The vascular imaging system of claim 1, further comprising:
at least a second light source configured to generate at least second coherent light having a wavelength different than that of the first coherent light such that the first coherent light and the second coherent light penetrate the target tissue to different extents.

18. The vascular imaging system of claim 16, wherein:
for any value of n between 1 and 100, the said one or more pixel intensities correspond to intensity of the said certain pixel in a certain image frame, intensities of a first plurality of pixels spatially adjacent to the certain pixel in a certain image frame, intensity of n pixels each obtained from n frames temporally adjacent to the certain image frame at a same spatial location as the certain pixel in a certain image frame, and intensities of n plurality of pixels spatially adjacent to each of the said n pixels in their respective n adjacent frames.

19. The vascular imaging system of claim 18, wherein the one or more processors are configured to calculate the laser speckle contrast value for said certain pixel by determining a square root of said square of laser speckle contrast value for said certain pixel.

20. The vascular imaging system of claim 18, wherein the one or more processors are configured to determine an estimate of blood flow at said certain pixel by representing said square of laser speckle contrast value with another unique set of values.

21. The vascular imaging system of claim 20, wherein the said another unique set of values is one or more of a single number, a percentage, or a set of numbers that represent a color scheme.

22. The vascular imaging system of claim 16, wherein one or more of a value in the first memory location, a value in the second memory location, a calculated square of a laser speckle contrast value, or a calculated laser speckle contrast value are updated when a new image frame is received by the processor from the image acquisition device.

23. The vascular imaging system of claim 22, wherein the value in the first memory location is updated by subtracting the sum of pixel intensities from pixels in the oldest image frame to reside at the first memory location and adding the sum of pixel intensities from spatially corresponding pixels in said new image frame.

24. The vascular imaging system of claim 22, wherein the value in the second memory location is updated by subtracting the sum of squares of pixel intensities from pixels in the oldest image frame to reside at the first memory location and adding the sum of squares of pixel intensities from spatially corresponding pixels in said new image frame.

25. The vascular imaging system of claim 20, wherein the unique set of values is updated when a new image frame is received by the processor from the image acquisition device.

26. The vascular imaging system of claim 14, wherein:
the anatomical information includes one or more of a diameter, tortuosity, depth in the target tissue, length, or type of the vessel; and
the physiological information includes one or more of blood flow, blood velocity, change in blood flow, change in blood velocity, or spatial distribution of blood flow in the vessel.

\* \* \* \* \*